US006811980B2

(12) United States Patent
Ford et al.

(10) Patent No.: US 6,811,980 B2
(45) Date of Patent: Nov. 2, 2004

(54) PROCESS FOR IMMOBILIZATION OF NUCLEIC ACID MOLECULES ON A SUBSTRATE

(75) Inventors: William E. Ford, Stuttgart (DE); Jurina Wessels, Fellbach (DE); Oliver Harnack, Stuttgart (DE)

(73) Assignee: Sony International (Europe) GmbH, Berlin (DE)

( * ) Notice: Subject to any disclaimer, the term of this patent is extended or adjusted under 35 U.S.C. 154(b) by 0 days.

(21) Appl. No.: 09/988,978

(22) Filed: Nov. 19, 2001

(65) Prior Publication Data

US 2002/0091245 A1 Jul. 11, 2002

(30) Foreign Application Priority Data

Nov. 20, 2000 (EP) .............................................. 00125433

(51) Int. Cl.[7] .......................... C12Q 1/68; C12P 19/34; C12M 1/34; C07H 21/02; C01H 21/04
(52) U.S. Cl. .......................... 435/6; 435/7.1; 435/91.1; 435/91.2; 435/287.2; 536/22.1; 536/23.1; 536/24.3; 521/53; 521/59; 521/84.1; 521/143; 521/146; 428/453; 428/543; 525/54.1
(58) Field of Search .......................... 435/6, 7.1, 91.1, 435/91.2, 287.2; 536/221, 231, 24.3–24.33; 521/146, 53, 59, 84.1, 143; 428/453, 543; 525/54.1

(56) References Cited

U.S. PATENT DOCUMENTS

| 5,369,012 | A | * | 11/1994 | Koontz et al. | .............. | 435/7.92 |
| 5,552,272 | A | | 9/1996 | Bogart | .......................... | 436/6 |
| 5,770,722 | A | * | 6/1998 | Lockhart et al. | ........... | 536/25.3 |
| 6,022,902 | A | * | 2/2000 | Koontz | ........................ | 521/53 |
| 6,060,288 | A | | 5/2000 | Adams et al. | .............. | 435/91.2 |

FOREIGN PATENT DOCUMENTS

| EP | 1 063 286 | 12/2000 |
| WO | WO 99 40173 | 8/1999 |

* cited by examiner

Primary Examiner—Jeffrey Siew
(74) Attorney, Agent, or Firm—Frommer Lawrence & Haug LLP; William S. Frommer; Samuel H. Megerditchian

(57) ABSTRACT

The present invention relates to a process for immobilization of nucleic acid molecules on a substrate, wherein the substrate is treated with atomic oxygen plasma prior to immobilizing the nucleic acid molecules thereon. The invention is further related to immobilized nucleic acid molecules and uses thereof.

13 Claims, 4 Drawing Sheets

PROCESS FOR IMMOBILIZATION OF NUCLEIC ACID MOLECULES ON A SUBSTRATE

DESCRIPTION

The invention relates to a process of immobilization of nucleic acid molecules on a substrate, immobilized nucleic acid obtainable therefrom and use thereof.

Immobilization (binding) of nucleic acid molecules on a substrate, such as a solid surface, is a well known problem in a large number of applications. The binding of nucleic acid molecules on substrates is of high interest for the development of nucleic acid based nanotechnology, including nucleic acid based nanoelectronics, like wires, biosensors, chips, see Storhoff, J. J., Mirkin, C. A. (1999) Chem. Rev., 99, 1849–1862 "Programmed Materials Synthesis with DNA."

Another strong motivation for immobilizing nucleic acid molecules on substrates and membranes is the characterization and engineering of nucleic acids in the field of medicine and biology, see Allison, D. P., Bottomley, L. A., Thundat, T., Brown, G. M., Woychik, R. P., Schrick, J. J., Jacobson, K. B. and Warmack, R. J. (1992) Proc. Natl. Acad. Sci. USA, 89,21 10129–10133 "Immobilization of DNA for scanning probe microscopy"; Bezanilla, M., Manne, S., Laney, D. E., Lyubchenko, Y. L. and Hansma, H. G. (1995) Langmuir, 11, 655–659 "Adsorption of DNA to mica, silylated mica and minerals: characterization by atomic force microscopy."

Also, purification of nucleic acid solutions by attachment of nucleic acid molecules to substrates is of interest, see U.S. Pat. Nos. 5,523,392 and 5,503,816.

The binding problem for nucleic acids to solid surfaces has so far been solved by using a number of different approaches.

The most common ones employ the modification of the substrate surface by chemical treatment. One useful approach is the silanization of surfaces leading, for example, to exposed vinyl groups which bind to nucleic acid molecules, see Bensimon, D., Simon, A. J., Croquette, V., Bensimon, A. (1995) Physical Review Letters 74, 23, 4754–4757 "Stretching DNA with a Receding Meniscus: Experiments and Models." On mica substrates, effective binding of the nucleic acid was found by using the counterion method: this method is done by adsorbing the nucleic acid onto mica in the presence of a divalent (+2 charged) ion, like $Mg^{2+}$. The idea is that the counterion will provide binding to the negatively charged nucleic acid backbone and at the same time also to the negatively charged mica surface, see Ye, J. Y., Umemura, K., Ishikawa, M., Kuroda, R. (2000) Analytical Biochemistry 281, 21–25 "Atomic Force Microscopy of DNA Molecules Stretched by Spin-Coating Technique."; Dunlap, D. D., Maggi, A., Soria, M. R., Monaco, L. (1997) Nucl. Acid Res. 25, 3095 "Nanoscopic Structure of DNA Condensed for Gene Delivery."; Lyubchenko, Y. L., Shlyakhtenko, L. S. (1997) Proc. Natl. Acad. Sci. USA 94,496 "Direct Visualization of Supercoiled DNA in situ with Atomic Force Microscopy."; Yokota, H., Sunwoo, J., Snikaya, M., van den Engh, G., Aebersold, R. (1999) "Spin-Stretching of DNA and Protein Molecules for Detection by Fluorescence and Atomic Force Microscopy."

Also, the adjustment of the degree of immobilization through the chemical control of the pH-value was described for a large variety of different surfaces, see Allemand, J.-F., Bensimon, D., Julien, L., Bensimon, A, Croquette, V. (1997) Biophysical Journal, 73, 2064–2070 "pH-Dependent Binding and Combing of DNA."

Yoshida, K., Yoshimoto, M., Sasaki, K., Ohnishi, T., Ushiki, T., Hitomik, J., Yamamoto, S., Sigeno, M. (1998) Biophysical Journal, 74, 1654–1657 "Fabrication of a New Substrate for Atomic Force Microscopic Observation of DNA Molecules from an Ultrasmooth Sapphire Plate." describes the hydrophilization of a sapphire surface treated with $Na_3PO_4$ aqueous solution. It is reported that the hydrophilic surface character after the wet treatment makes it easy for nucleic acid molecules to adhere to the substrate surface. Other approaches utilize the specific binding (chemisorption) of thiol-group terminated nucleic acid to gold surfaces and electrodes. Washizu, M., Kurosawa, O., Arai, I., Suzuki, S., Shimamoto, N. (1995) IEEE Trans. Industr. Appl., 31, 3, 447–456 "Applications of Electrostatic Stretch-and-Positioning of DNA." reported on strong, covalent-like binding of nucleic acids to fresh aluminum electrodes in an alternating electrical field.

Oxygen plasma treatment is a well-known method to clean surfaces from organic impurities by oxidation, which supports the generation of OH-groups. U.S. Pat. No. 5,055, 316 teaches the oxygen plasma supported tight binding of proteins to surfaces. Molecular tailoring of surfaces using a plasma treatment is disclosed in U.S. Pat. No. 5,876,753. A method of making a membrane having hydrophilic and hydrophobic surfaces for adhering cells or antibodies by using atomic oxygen or hydroxyl radicals was described in U.S. Pat. No. 5,369,012.

As mentioned above, various nucleic acid immobilization methods have been proposed. Most of them employ wet chemical treatment to modify the substrate. Therefore, the use of expensive chemical components is necessary, often not providing reproducible and permanent immobilization of nucleic acid molecules on that substrate.

Only a small variety of substrate materials can be employed using the above mentioned wet chemical treatment.

Accordingly, it is an object of the present invention to provide a process for immobilization of nucleic acid molecules on a substrate to overcome the drawbacks of prior art, especially to provide a process not requiring a wet chemical treatment of the substrate and to provide a reproducible process for the permanent immobilization of nucleic acid molecules on a substrate.

A further object underlying the present invention is to provide an immobilized nucleic acid which may be used in nucleic acid based nanotechnology.

The first object is solved by a process for immobilization of nucleic acid molecules on a substrate wherein the substrate is treated with atomic oxygen plasma prior to immobilizing the nucleic acid molecules thereon.

In a preferred embodiment the nucleic acid is selected from the group consisting of DNA,RNA, PNA (peptidic-NA), CNA (aminocyclohexylethane acid-NA), HNA (hexitol nucleic acids), p-RNA (pyranosyl-RNA), oligonucleotides, oligonucleotides of DNA, oligonucleotides of RNA, primers, A-DNA, B-DNA, Z-DNA, polynucleotides of DNA, polynucleotides of RNA, T-junctions of nucleic acids, domains of non-nucleic acid polymer-nucleic acid blockpolymers and combinations thereof. Suited non-nucleic acid polymers for blockcopolymers can be polypeptides, polysaccharides such as cellulose, or artificial polymers, such as polyethylene glycol, and are generally known to the person skilled in the art.

In another embodiment the nucleic acid is double-stranded or single-stranded.

In a further embodiment the nucleic acid is of natural character, modified, such as substituted with functional groups, non-modified or artificially generated.

In a still further embodiment the substrate is a single crystal surface or an amorphous surface.

More preferably the surface material is selected from the group comprising silicon oxides, glass, aluminum oxides, sapphire, perovskites, like $SrTiO_3$, $LaAlO_3$, $NdGaO_3$, $ZrO_2$ and derivatives thereof and doped and/or stabilized derivatives thereof, for example using Yttrium as stabilizer.

In a further preferred embodiment microwave generated oxygen plasma producing atomic oxygen or mixtures of gases containing oxygen are used. Preferred gases for admixture are all noble gases.

Alternatively high-voltage generated and/or UV-light emitting source generated oxygen plasma producing atomic oxygen or mixtures of gases containing oxygen are used.

Still a further embodiment is characterized in that the substrate is treated with atomic oxygen plasma for about 0.1 to 10 minutes.

It is preferred that the atomic oxygen plasma treatment is carried out using an oxygen pressure in the range of about 0.1 to 1.0 mbar, preferably 0.2 to 0.8 mbar.

The immobilization of the nucleic acid to the substrate can be adjusted by changing the intensity and duration of the plasma treatment. For example, using short time/low pressure conditions ($p_{O2}$=0.4 mbar, t=4 mn) leads to a weak binding of DNA molecules to the surface, whilst using long-time/high-pressure conditions ($p_{O2}$=0.8 mbar, t=8 mn) leads to a high density and strong binding of DNA molecules to the surface. These parameters correspond to a high-voltage power of 33 Watts at a frequency of 50 Hz. In the hands of the inventors these parameters lead to optimal results in terms of the cost to benefit-ratio. The pressures and times given here are meant as non-limiting examples of the invention. In fact, higher power levels can be used to reduce the minimum process time required to observe a significant binding effect. The individual protocols will vary depending on the machinery and the setup used for the immobilization process but can easily be determined by the person skilled in the art employing the general concept of the invention.

In a still further embodiment the nucleic acid to be immobilized on the substrate is present in an aqueous solution, for example a biological buffer solution.

Moreover it is preferred that the substrate is treated with the nucleic acid containing aqueous solution for at least a few seconds up to 5 minutes, preferably 1 to 2 minutes.

The second object is solved by an immobilized nucleic acid obtainable by a process according to the present invention.

In a still further aspect the object is solved by the use of the immobilized nucleic acid prepared according to the process of the present invention in nucleic acid based nanotechnology, such as nanoelectronics, like wires, biosensors, chips and the like.

Surprisingly, it was found that the process of the present invention is adjustable, highly reliable and fast, leads to long-term stable immobilization of nucleic acid molecules on various substrates, and is inexpensive. Moreover, the surface does not require any chemical treatment prior immobilization of nucleic acids thereon and therefore, the process of the present invention does not generate chemical waste. Additionally, it was surprisingly found that the process of the present invention is controllable in terms of the degree of immobilization of nucleic acid molecules. By changing the intensity and the duration of the plasma treatment the density of the nucleic acid molecules on the substrate surface and the density of binding sites is adjustable. The process of the present invention discloses a dry surface treatment to provide immobilization of nucleic acid molecules on a surface.

Also, it was surprisingly found that the immobilized nucleic acid obtainable by the process of the present invention can be used in nucleic acid based nanotechnology, such as nanoelectronics.

The nucleic acid herein referred to also as nucleic acid molecule may be either DNA or RNA. This interchangeability, which applies to many cases, resides in physiochemical similarities between DNA and RNA. Of course, any nucleic acids or derivatives thereof can also be used in the present invention such as, but not limited to, oligonucleotides of DNA and RNA, respectively, primers thereof and polynucleotides of each of said two nucleic acid species. Additionally, nucleic acids which can be used in the present invention may show various confirmations such as A-DNA, B-DNA and Z-DNA which differ mostly in the diameter and the particular kind of helix structure. Also domains of nucleic acids within larger units may be used. It is to be understood that any of the aforementioned nucleic acid species may be either in a double-stranded or single stranded form.

The invention is now further illustrated by the following detailed description and the accompanying figures from which further embodiments, features and advantages may be taken.

SAMPLE PREPARATION

Figure 1:
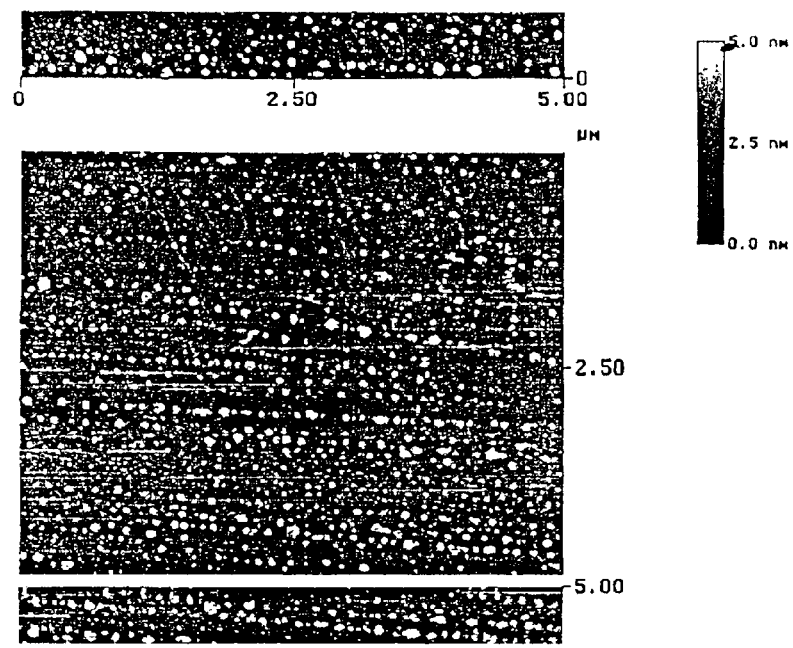
FIG. 1 shows an AFM picture of DNA on an untreated sapphire surface.

All experimental results provided in the following section were achieved by using calf thymus (ct) DNA molecules, commercially available from Sigma, Taufkirchen, Germany. DNA was diluted in a biological buffer N-[2-hydroxyethyl] piperazine-N'-[2-ethanesulfonic acid] (HEPES), commercially available from Sigma, Taufkirchen, Germany, to obtain an optical density of 0.093 at 258 nm wavelength and at 1 cm path length. The plasma processor used was a "PlasmaPrep5" machine manufactured by Gala Instruments, Bad Schwalbach, Germany. Detailed experimental examples will be given for sapphire, silicon, and glass substrates. The parameter for the plasma duration, the electrical power or microwave power used to generate the oxygen plasma, and the oxygen plasma have to be adjusted for each technical setup and each substrate system. Here, the process parameters based on the particular equipment will be given and the tendencies of the variation of the immobilization effect with the process parameters will be shown.

The Process of the present invention is done as follows:

Step 1

The substrate surface is cleaned in an acetone and propanol bath and then blown dry by compressed air or nitrogen gas.

Step 2

The substrate is then inserted into a vacuum chamber, which will be evacuated and filled with pure oxygen gas to reach an oxygen pressure of $p_{O2}$.

Step 3

At an oxygen pressure $P_{O2}$ usually in the range between 0.1 and 1 mbar the oxygen plasma was ignited. The duration t of the plasma treatment depends on the substrate material. Table 1 below gives an overview of typical process parameters for sapphire, silicon, and glass. It has to be mentioned that these parameters do depend on the specific setup. In general, too short treatments lead to a weak immobilization effect and too long treatment causes heating of the sample, which also reduces the immobilization effect. The minimum process time characterizes the amount of time which is necessary to observe a clear binding effect of the nucleic acid (in this case DNA) to the surface. Depending on the plasma conditions, this time is of the order of a few seconds. However, the creation of binding sites by the plasma starts immediately after the plasma is switched on. In fact, the generation of a minimal density of binding state which is required to effectively bind the investigated type of nucleic acid molecules (in this case DNA) requires only a few seconds.

TABLE 1

| Substrate | duration of plasma treatment (min) | oxygen pressure (mbar) |
|---|---|---|
| Sapphire | 1–2 | 0.2–0.4 |
| Silicon | 4–6 | 0.4–0.8 |
| Glass | 4–6 | 0.4–0.8 |

Step 4

The sample surface is treated with 1 to 2 drops of DNA in HEPES buffer, which immediately coats the entire substrate surface. After at least 1–2 minute treatment time the sample is spin-dried at 1,000 to 5,000 rpm to remove the liquid component of the DNA/HEPES solution. Afterwards, the surface is washed with a few drops deionized water in order to remove salt components of the HEPES buffer.

Surface Investigations

The processed sample surface was usually investigated using an atomic force microscope (AFM), Model NanoScope IIIa, Digital Instruments, Santa Barbara, Calif., USA.

FIG. 1 shows an AFM picture of the resulting surface of sapphire substrate, which was processed by applying Step 4 only. The picture shows a high density of coiled-up DNA molecules, which are not effectively immobilized, on the surface, but easy to remove by additional wash cycles with water. Also, the fact that only very few molecules are elongated and most of the molecules are not elongated, but coiled-up, indicates that no effective binding of DNA molecules to the substrate takes place.

Figure 2:
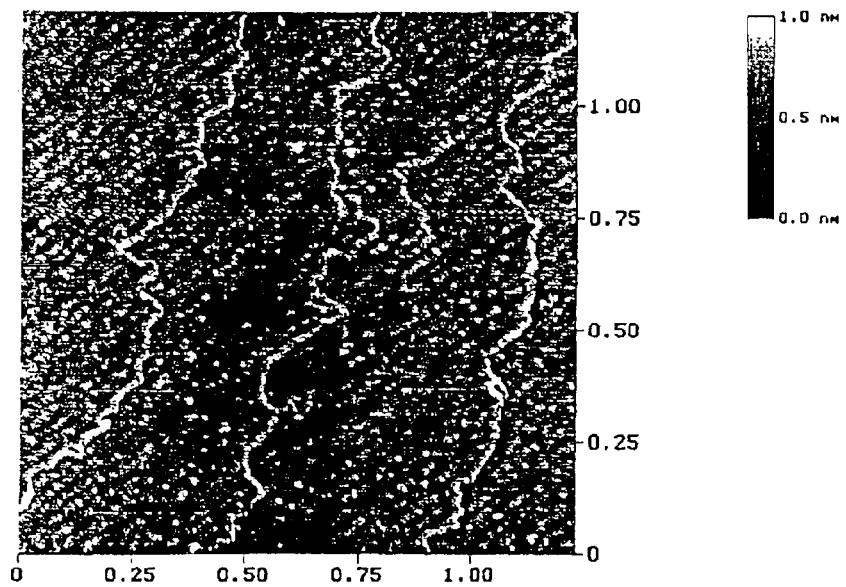
FIG. 2 illustrates an AFM picture of DNA on a sapphire surface treated according to the process of the present invention.

FIG. 2 shows an AFM picture of a sapphire substrate surface, which was treated by applying Step 1 to Step 4 using parameters as given in Table 1 above. Single wellstretched DNA molecules become visible. The fact that the molecules are not coiled-up and that they are not easy to remove by wash cycles in water suggest an enhanced binding of DNA to the substrate surface.

The same observation was done for silicon and glass surfaces.

Figure 3:
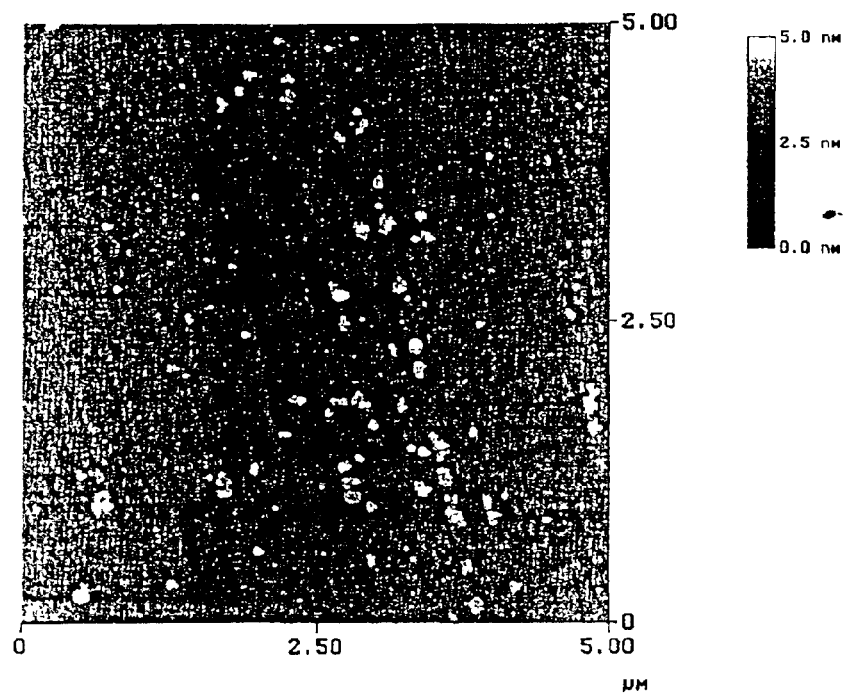
FIG. 3 shows an AFM picture of DNA on an untreated silicon surface.
Figure 4:
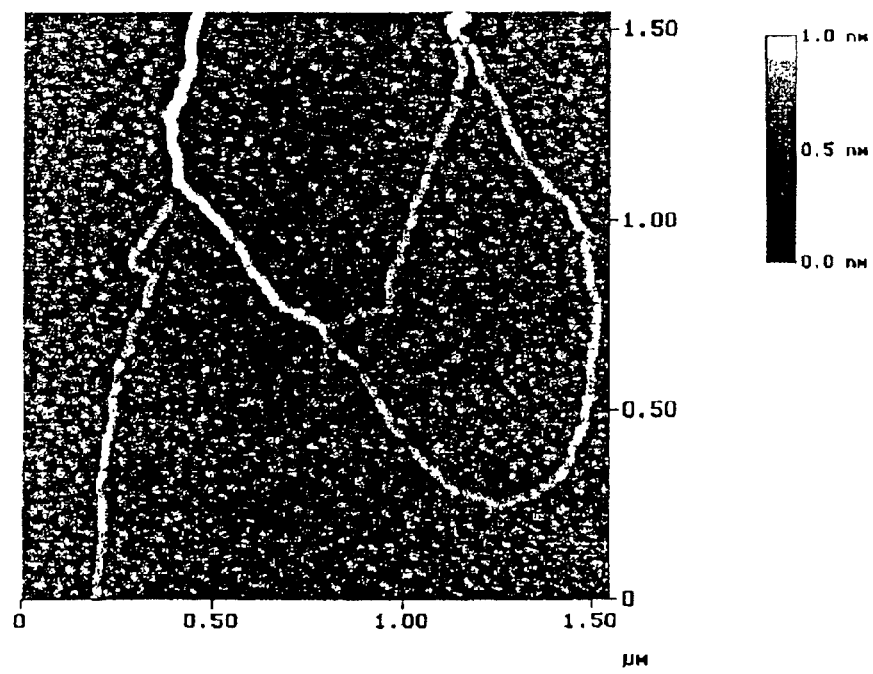
FIG. 4 shows an AFM picture of DNA on a silicon surface treated according to the process of the present invention.

FIG. 3 shows an AFM picture of a silicon surface treated by applying Step 4 only. A similar situation as shown in FIG. 1 was found. No significant immobilization effect of DNA was observed. In contrast to this, the silicon surface, treated by applying Step 1 to Step 4 in respect to the process parameters given in Table 1 above shows a clear immobilization effect of DNA (see FIG. 4). This is clearly consistent with the above-mentioned results on sapphire.

In summary, the process of the present invention demonstrates that the use of atomic oxygen plasma strongly enhances binding of nucleic acid molecules to various solid surfaces and that a control in terms of the degree of immobilization of nucleic acid molecules is possible by adjusting the plasma process parameters.

The immobilization effect can be quantified in terms of the final density of nucleic acid effectively immobilized on the surface and the degree of binding which presumably is proportional to the density of binding sites. The density can be estimated by looking at AFM pictures and the degree of binding can be qualitatively estimated from the final shape of the immobilized nucleic acid molecules on the surface.

Figure 5:
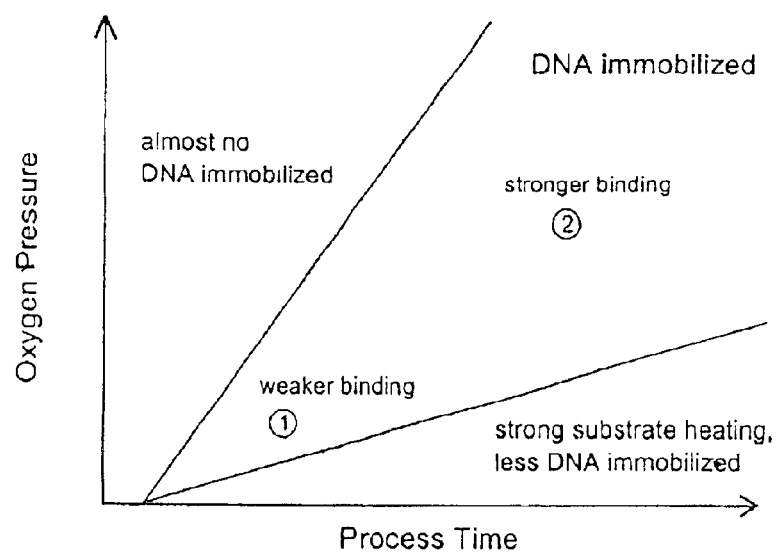
FIG. 5 illustrates a diagram showing qualitatively the variation of the DNA immobilization effect with the process parameter oxygen pressure and time.

FIG. 5 summarizes the general trends of the process results when the plasma duration and the oxygen pressure are changed.

First of all, there is a lower limit for the process time in order to obtain a significant immobilization effect. Below a certain period of time no significant immobilization effect is found. In this regime a clearer immobilization effect can be found if the oxygen pressure is lowered. Beyond this limit a too high and a too low oxygen pressure causes less effective immobilization of DNA. There is an intermediate range where the immobilization of DNA is highly effective. In this range it was experimentally found that the degree of binding roughly increases with time and with oxygen pressure.

Figure 6:
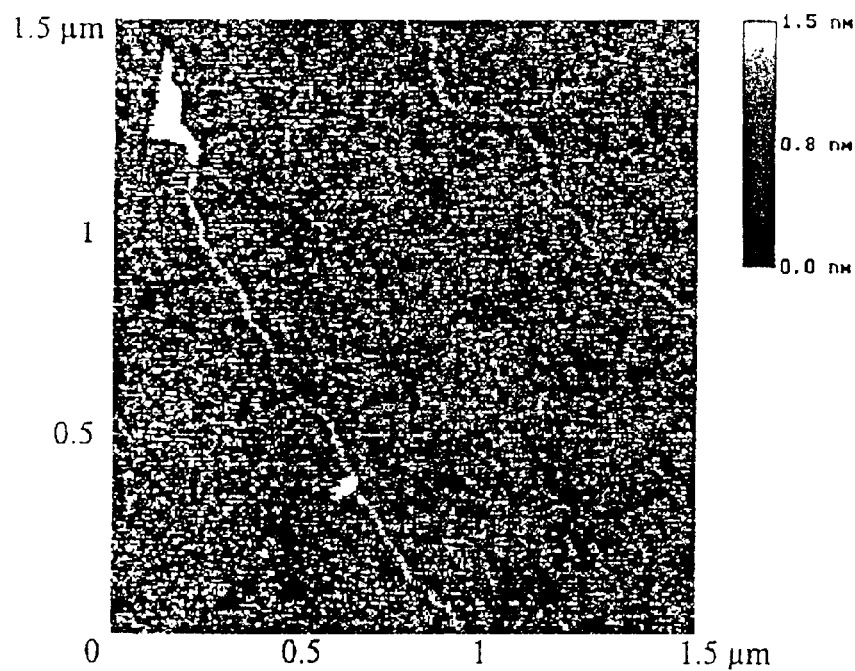
FIG. 6 shows an AFM picture of DNA immobilized on silicon.
Figure 7:
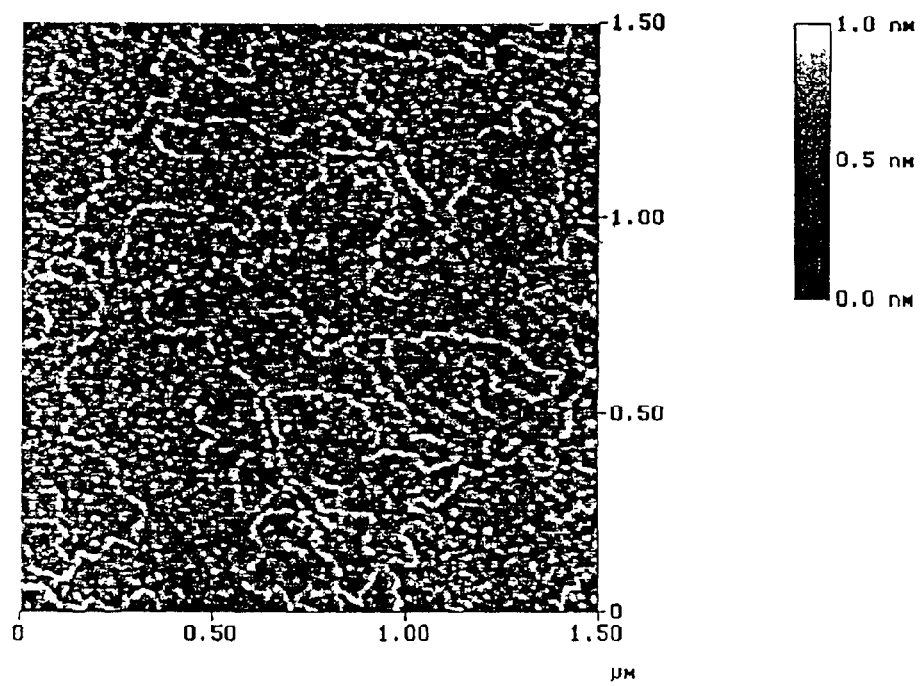
FIG. 7 shows a further AFM picture of DNA immobilized on silicon.

A demonstration of this tendency is provided in FIG. 6 and FIG. 7. In both cases DNA was immobilized on silicon substrates.

FIG. 6 shows an AFM picture of immobilized DNA on a surface which was treated using a short time/low pressure regime ($p_{O2}$=0.4 mbar, t=4 min) as indicated by circled "1" in FIG. 5. This procedure leads to a weak binding of DNA molecules to the surface.

FIG. 7 shows an AFM picture of immobilized DNA on a similar surface which was treated using a long-time/high-pressure regime ($p_{O2}$=0.8 mbar, t=8 min) as indicated by circled "2" in FIG. 5. A high density and strong binding of DNA molecules to the surface was found.

The fact that in FIG. 7 more DNA molecules per unit are found than in FIG. 6 and that in FIG. 7 the DNA molecules are less stretched, but more attached in a zig-zag-like shape supports the idea that the regime "2" leads to a higher binding energy, thus to a more effective immobilization of DNA.

The features of the present invention disclosed in the specification, the claims and/or the accompanying drawings may both separately and in combination thereof be material for realizing the invention in various forms thereof.

What is claimed is:

1. A process for immobilizing nucleic acid molecules on a substrate, comprising the steps of:
  a) treating said substrate with atomic oxygen plasma prior to immobilizing said nucleic acids; and
  b) immobilizing said nucleic acid molecules on said treated substrate, wherein said substrate is a single crystal surface or an amorphous surface selected from the group consisting of silicon oxides, aluminum oxides, sapphire, perovskites, and derivatives and stabilized and/or doped derivatives thereof.

2. The process according to claim 1, wherein the nucleic acid is selected from the group consisting of DNA, RNA, PNA, CNA, RNA, HNA, p-RNA, oligonucleotides, oligonucleotides of DNA, oligonucleotides of RNA, primers, A-DNA, B-DNA, Z-DNA, polynucleotides of DNA, polynucleotides of RNA, T-junctions of nucleic acids, domains of non-nucleic acid polymer-nucleic acid blockpolymers and combinations thereof.

3. The process according to claim 1, wherein the nucleic acid is double-stranded or single-stranded.

4. The process according to claim 1, wherein the nucleic acid is of natural character, modified, such as substituted with functional groups, non-modified or artificially generated.

5. The process according to claim 1, wherein microwave generated oxygen plasma producing atomic oxygen from an oxygen gas or from a mixture of gases containing oxygen is used.

6. The process according to claim 1, wherein high-voltage generated and/or UV-light emitting source generated oxygen plasma producing atomic oxygen from an oxygen gas or from a mixture of gases containing oxygen is used.

7. The process according to claim 1, wherein the atomic oxygen plasma treatment is carried out using an oxygen pressure in the range of about 0.1 to 1.0 mbar.

8. The process according to claim 1, wherein the nucleic acid to be immobilized on the substrate is present in an aqueous solution.

9. The process according to claim 8, wherein the substrate is treated with said aqueous solution for about a few seconds to about 5 minutes.

10. The process according to claim 1, wherein the perovskites are selected from the group consisting of $SrTiO_3$, $LaAlO_3$ and $ZrO_2$.

11. The process according to claim 7, wherein the pressure range is from about 0.2 to 0.8 mbar.

12. The process according to claim 9, wherein the substrate is treated with said aqueous solution for about 1 to 2 minutes.

13. The process according to claim 1, wherein the substrate is treated with atomic oxygen plasma for about 0.1 to 10 minutes.

* * * * *